United States Patent [19] [11] 4,400,168
Buechel et al. [45] Aug. 23, 1983

[54] ADJUSTABLE SURGICAL SUCTION APPARATUS

[75] Inventors: Frederick F. Buechel, Irvington; Michael J. Pappas, Caldwell; Paul A. Witte, Hopewell, all of N.J.

[73] Assignee: Biomedical Engineering Corp., Red Bank, N.J.

[21] Appl. No.: 308,773

[22] PCT Filed: May 7, 1981

[86] PCT No.: PCT/US81/00605
§ 371 Date: Sep. 8, 1981
§ 102(e) Date: Sep. 8, 1981

[87] PCT Pub. No.: WO81/03125
PCT Pub. Date: Nov. 12, 1981

Related U.S. Application Data

[63] Continuation-in-part of Ser. No. 148,042, May 8, 1980, abandoned.

[51] Int. Cl.³ .................. A61M 31/00; A61M 1/06
[52] U.S. Cl. .................................. 604/48; 604/73; 604/93; 433/95
[58] Field of Search ............ 128/276, 305, 752, 753, 128/754, 758; 30/133; 15/344, 345, 416, 417, 418, 419; 604/19, 22, 27, 30, 33, 35, 36, 48, 93, 73, 289; 222/522, 523; 83/402, 451; 433/91, 95

[56] References Cited

U.S. PATENT DOCUMENTS

| 950,109 | 2/1910 | Levkowicz | 433/91 |
| 3,169,528 | 2/1965 | Knox et al. | 433/91 |
| 3,173,414 | 3/1965 | Guillant | 128/752 |
| 3,777,743 | 12/1973 | Birnard et al. | 128/305 |
| 3,863,635 | 2/1975 | Swatman | 128/276 |
| 4,011,869 | 3/1977 | Seiler, Jr. | 604/22 |
| 4,031,896 | 6/1977 | Ronnmark | 128/276 |
| 4,049,002 | 9/1977 | Kletsonka et al. | 604/22 |
| 4,307,720 | 12/1981 | Weber, Jr. | 128/303.18 |

FOREIGN PATENT DOCUMENTS

| 258116 | 4/1912 | Fed. Rep. of Germany | 128/276 |
| 2362157 | 11/1974 | Fed. Rep. of Germany | 128/305 |
| 350405 | 7/1937 | Italy. | |
| 29038 | of 1913 | United Kingdom | 15/418 |
| 2018601 | 10/1979 | United Kingdom | 128/305 |

OTHER PUBLICATIONS

"Cannula for Emptying the Small Bowel in Cases of Intestinal Obstruction", Pampari et al., Surgery, vol. 30, Issue 6, pp. 944-949, Dec. 1951.

Primary Examiner—Richard J. Apley
Assistant Examiner—J. L. Kruter
Attorney, Agent, or Firm—R. Gale Rhodes, Jr.

[57] ABSTRACT

Surgical suction apparatus for applying suction to surgical debris to clear a surgical wound and including structure for clearing any surgical debris lodged in the entrance aperture of the apparatus and which structure may also be used to vary the effective size of the entrance aperture to vary the suction applied to the surgical debris.

13 Claims, 10 Drawing Figures

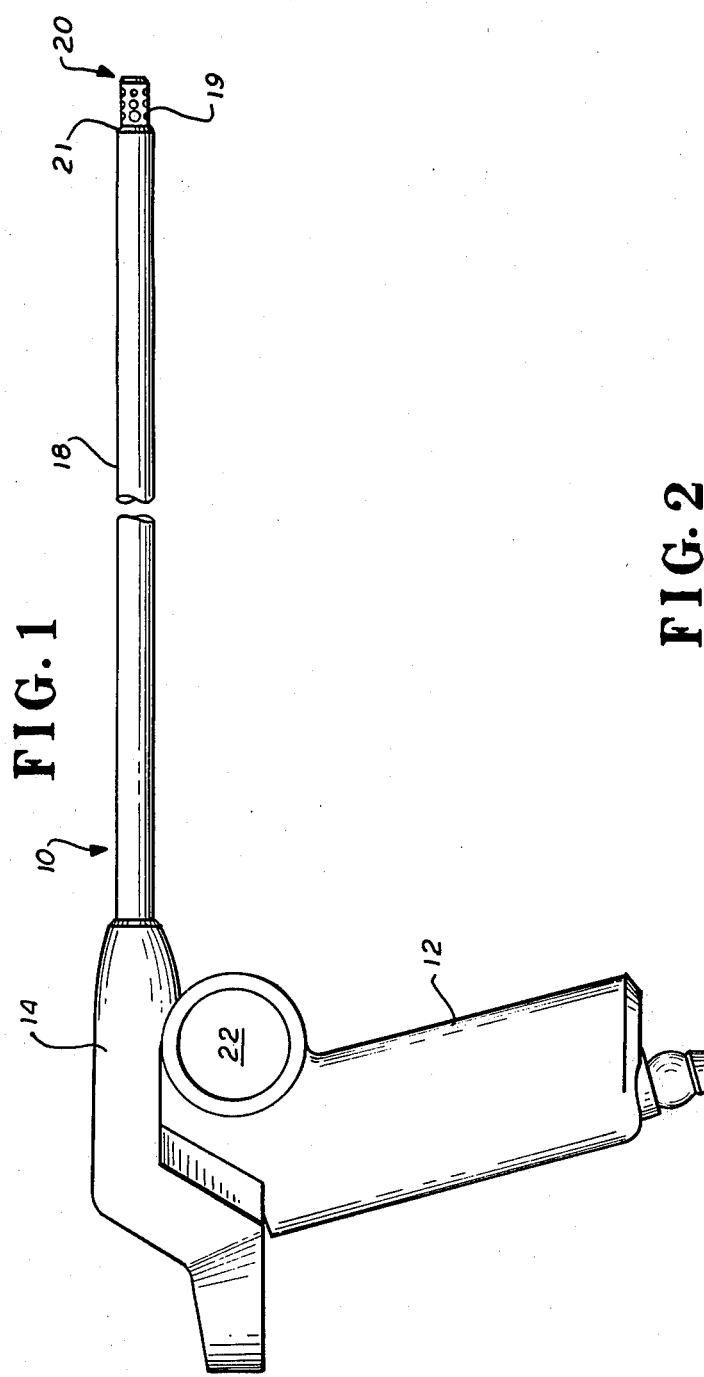
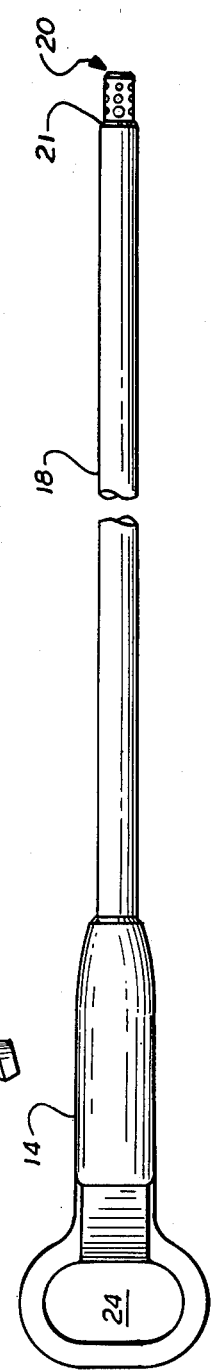

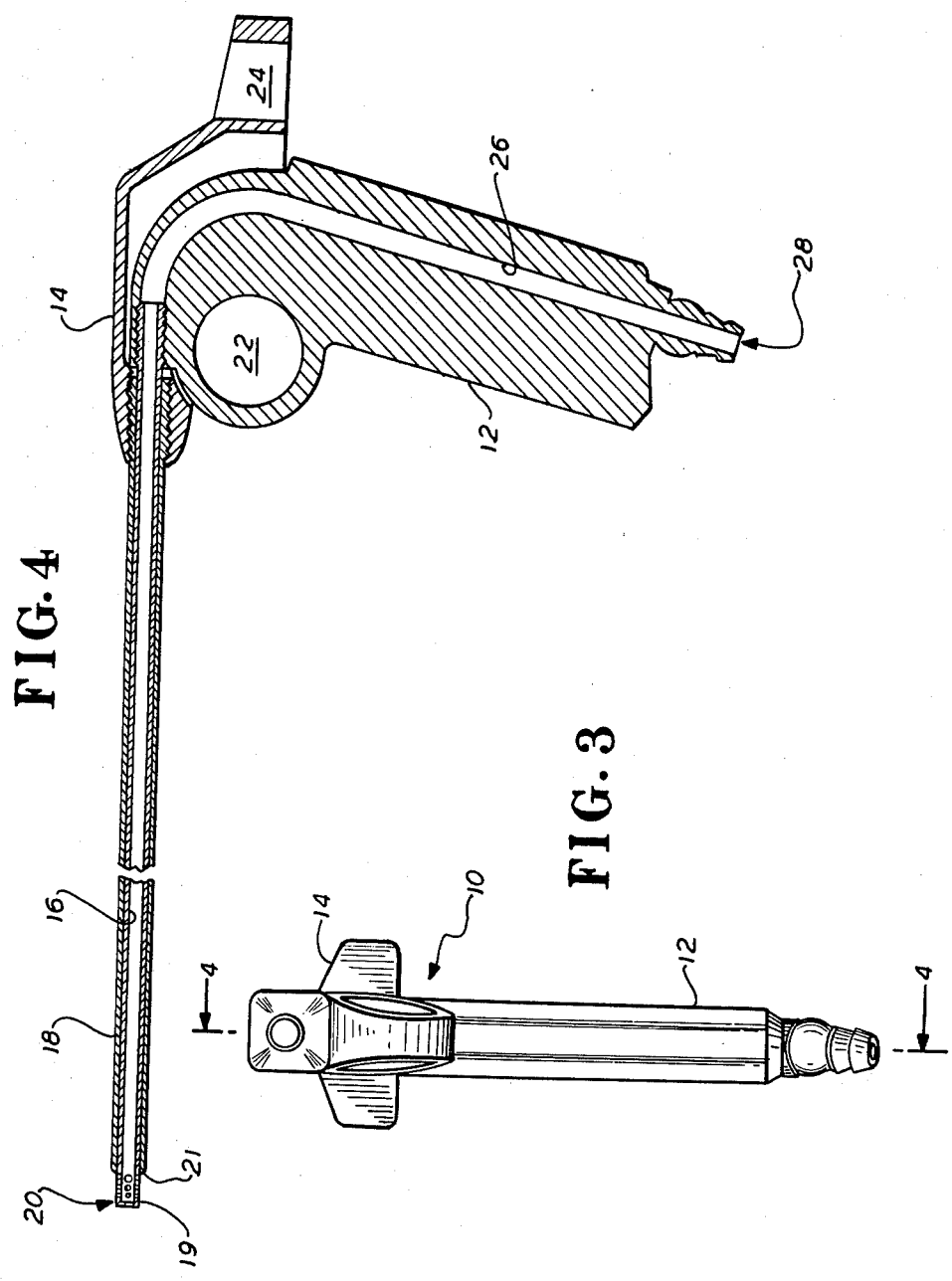

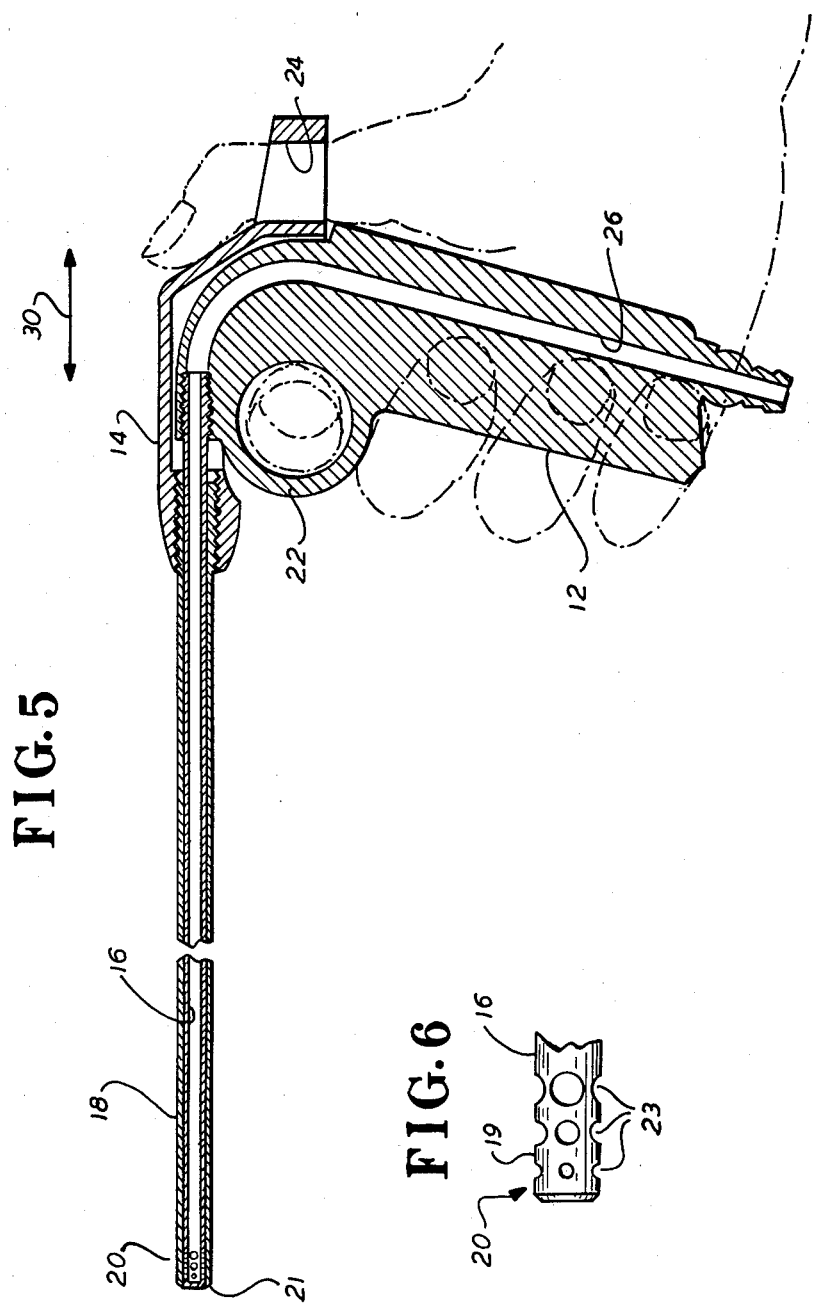

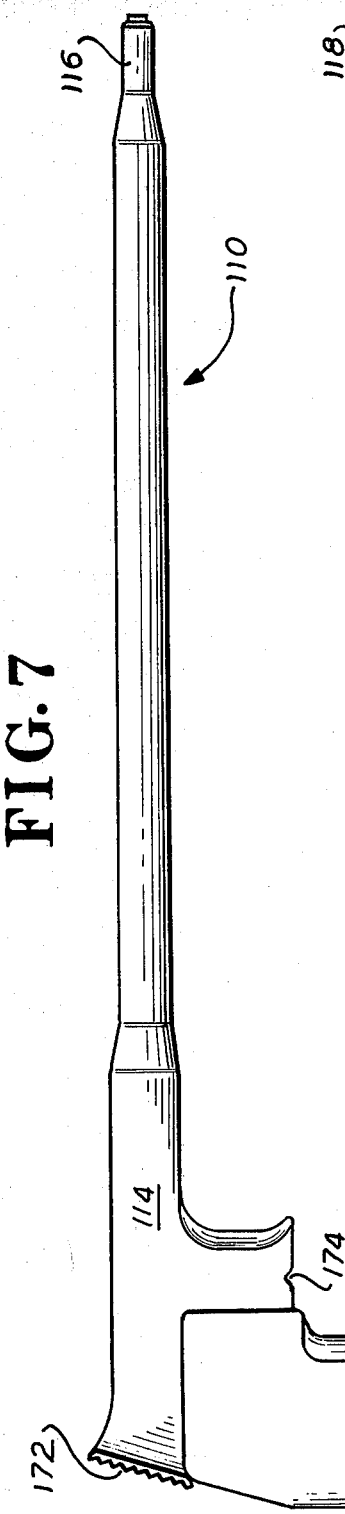
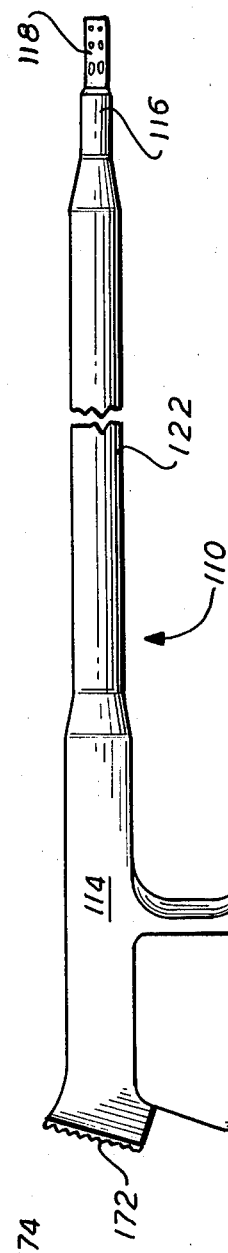
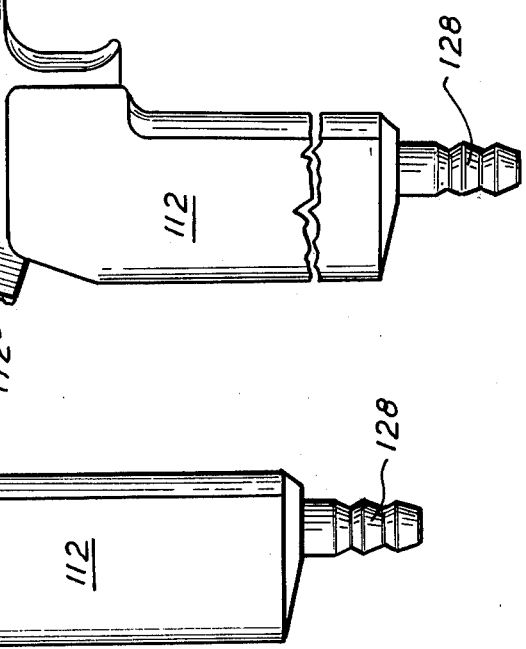

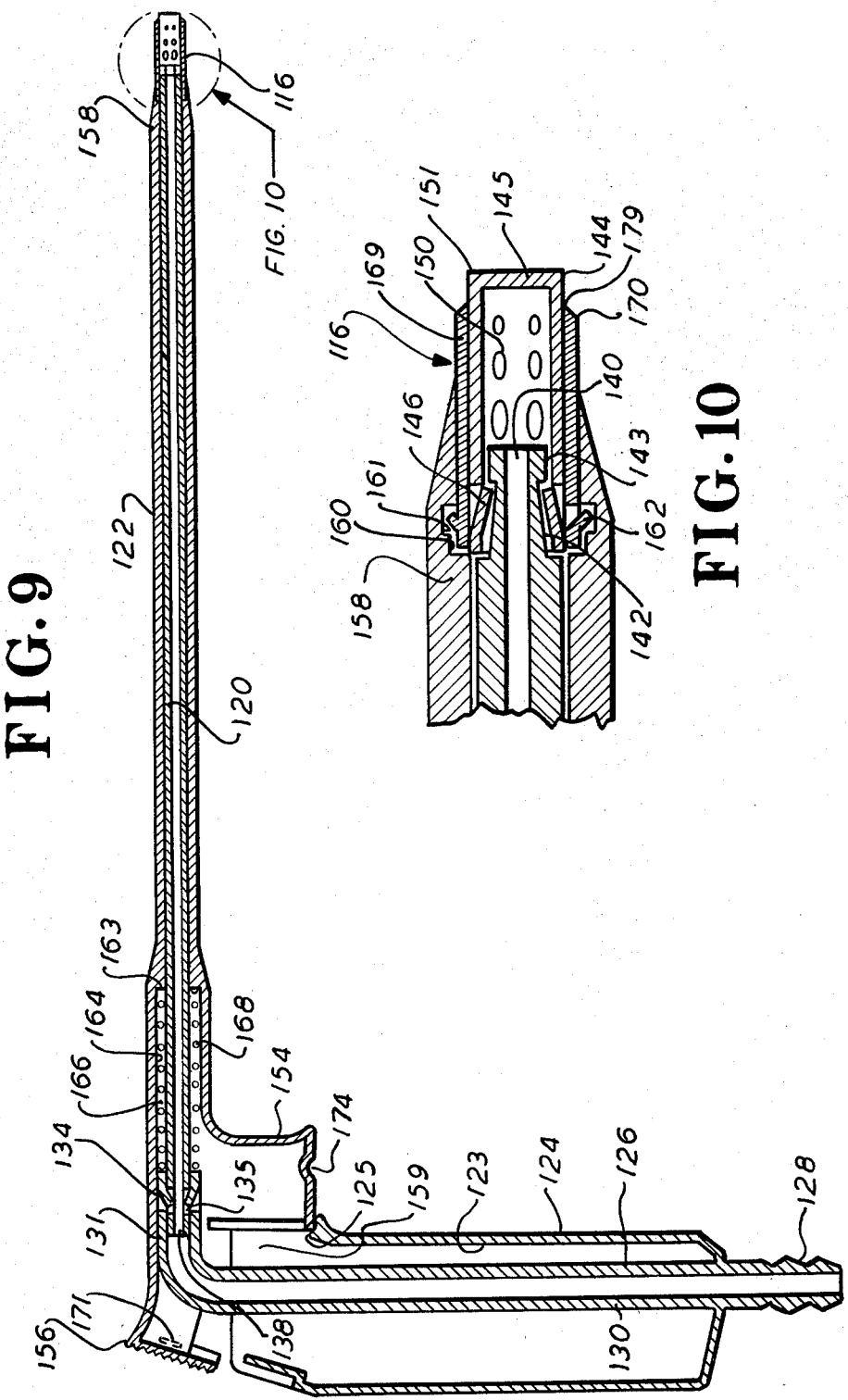
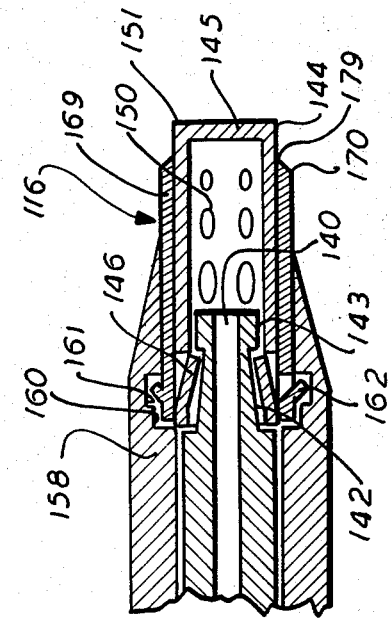
FIG. 9
FIG. 10

ADJUSTABLE SURGICAL SUCTION APPARATUS

CROSS REFERENCE TO RELATED APPLICATION

This application is a continuation-in-part application of an earlier filed application, Ser. No. 148,042, of the same inventors, filed May 8, 1980, now abandoned.

TECHNICAL FIELD

This invention relates to surgical suction apparatus for clearing a surgical wound of surgical debris, such as, blood, irrigation solutions, fragments of soft and hard (e.g. bone) tissue.

BACKGROUND ART

Surgical suction apparatus are routinely used in surgical procedures. A typical prior art surgical suction apparatus includes a suction tube having one end connected to a suction source and the other end serving as an entrance aperture into which surgical debris is sucked to clear a surgical wound. Clogging or blocking of the surgical suction apparatus, at the entrance aperture and/or along the length of the suction tube, are major problems with the typical prior art surgical suction apparatus. Such clogging or blocking results primarily from the cohesion of relatively hard fragments of tissue bound together by fragments of soft tissue. In the course of a typical surgical procedure, there may be several occurrences of such clogging or blocking and each such blockage results in an unwanted delay of time to clear the apparatus in a situation where elapsed time is usually critical.

Accordingly, there exists a need in the surgical suction apparatus art of new and improved surgical suction apparatus overcoming the clogging or blocking problem.

There exists a further need in the surgical suction apparatus art of new and improved surgical suction apparatus for varying the size of the entrance aperture to vary the suction applied to surgical debris.

Still further, there exists a need in the surgical suction apparatus art of new and improved surgical suction apparatus for both overcoming the clogging and blocking problem and for varying the suction applied to surgical debris.

A still further problem generally present with typical prior art surgical suction apparatus is that they remain in an open condition during an entire operation including time between actual use when not in the operator's hand. Air is therefore drawn through the surgical suction apparatus at all times thereby attracting bacteria laden air to the immediate vicinity of the operation from remote corners of the operating room where other equipment and observers are sometimes present and which other equipment and observers may not have received attention during pre-operative sterilization.

Accordingly, there exists a further need in the surgical suction apparatus art of new and improved surgical suction apparatus which may be closed or shut-off during periods of non-use.

SUMMARY OF THE INVENTION

The surgical suction apparatus of the present invention overcomes the above-noted prior art problem by including structure for clearing any surgical debris lodged in the entrance aperture of the apparatus and which structure may also be used to vary the suction applied to the surgical debris through the entrance aperture. The structure for clearing surgical debris lodged in the entrance aperture may be provided further with a cutter blade for engaging and cutting surgical debris lodged in the entrance aperture to enhance the clearing of the entrance aperture.

BRIEF DESCRIPTION OF THE DRAWINGS

FIGS. 1, 2 and 3 are, respectively, side elevational, plan and end views of surgical suction apparatus embodying the present invention;

FIGS. 4 and 5 are cross-sectional views showing the actuator means of the surgical suction apparatus of the present invention at its extreme rearward and forward positions, respectively;

FIG. 6 is an enlarged partial view of the forward end of an internal control tube illustrating the manner in which a plurality of radially disposed suction holes may be of different sizes;

FIG. 7 is a side elevational view of a second embodiment of the apparatus showing the apparatus in nonsuctioning mode;

FIG. 8 is a view similar to FIG. 7 but showing apparatus in suctioning mode;

FIG. 9 is a cross-sectional elevational view of apparatus configured as shown in FIG. 7; and FIG. 10 is an enlarged view of the distal end of the apparatus shown in FIG. 9.

DETAILED DESCRIPTION OF THE INVENTION

Referring now generally to FIGS. 1, 2 and 3, there is shown surgical suction apparatus embodying the present invention and being indicated by general numerical designation 10. Such apparatus may include a hand grip 12 to be gripped by the palm and lower three fingers of a single hand of an operator; an actuator 14 mounted slidably on top of the hand grip for sliding, reciprocating, translating movement with respect thereto; an internal suction tube 16 having its rearward portion secured to the hand grip 12 such as by being threadedly engaged therewith as indicated in FIGS. 4 and 5, and an external control tube 18 coaxially surrounding the internal suction tube 16 and having its rearward portion threadedly secured to the actuator 14 for sliding, reciprocating, translating movement with the actuator 14 and with respect to the hand grip 12 and the internal suction tube 16.

It will be noted that the suction tube 16 may be terminated at its forward end in a generally cylindrical filter 19 defined by a plurality of radially disposed suction holes (identified as 23 in FIG. 6), as shown, which suction holes provide an entrance aperture, indicated by general numerical designation 20, to the surgical suction apparatus 10 and into which entrance aperture surgical debris is sucked into the surgical suction apparatus. Further, it will be noted that the forward end of the control tube 18 may be terminated in a generally annular cutter blade 21.

As may be best seen in FIGS. 1 and 5, the hand grip 12 provides an aperture 22 for receiving the index finger of an operator's hand, and it will be noted, and as may be best seen in FIGS. 2 and 5, that the actuator 14 provides an aperture 24 for receiving the upwardly extending thumb of the operator.

Referring now to FIG. 4, it will be noted that the hand grip 12 is provided with a passageway 26 extending therethrough and that the upper portion of the passageway is connected to the rearward portion of the suction tube 16 and that the lower portion of the passageway 26 provides an exit aperture, indicated by general numerical designation 28, to the surgical suction apparatus 10 and through which exit aperture surgical debris exits the surgical suction apparatus. The exit aperture 28 of the surgical suction apparatus 10 is for being connected to a suitable suction source (not shown) and it will be further noted that the lower portion of the hand grip 12 defining the exit aperture 28 may be configured as shown to facilitate connection to a flexible hose (not shown) for extending between the surgical suction apparatus 10 and the suction source.

To understand the method of assembly of the parts of the embodiment of the surgical suction apparatus 10 shown, it will be assumed that the hand grip 12, actuator 14, internal suction tube 16 and external control tube 18 are all disassembled. Referring again to FIG. 4, the actuator 14 is first placed over the top of the hand grip 12, it being noted that the middle portion of the actuator is hollow and will be understood that this portion is substantially of an inverted U-shaped, cross sectional configuration, and the rearward portion of the internal suction tube 16 will be inserted through the forward portion of the actuator 14 to threadedly engage the rearward portion of the suction tube 16 with the threaded upper portion of the hand grip 12 defining the upper end of the passageway 26 as shown. Then, the external control tube 18 will be slid coaxially over the internal suction tube 16 and the rearward portion of the control tube 18 will threadedly engage the threaded forward portion of the actuator 14 as shown. For operation, a flexible hose then will be interconnected between the surgical suction apparatus 11 and the suction source as described above.

In operation, and referring to FIG. 5, a single hand of the operator will grip the surgical suction apparatus 10 as shown, with the hand grip being gripped by the palm and lower three fingers of the operator's hand, with the index finger of the operator's hand extending through the aperture 22 and with the thumb of the operator's hand being extended upwardly through the aperture 24. The entrance aperture 20 of the surgical suction apparatus 10 will then be inserted into a surgical wound and surgical debris will be sucked into the entrance aperture 20, through the internal suction tube 16 and passageway 26 and out the exit aperture 28. Then, the operator will alternately move his thumb forwardly and rearwardly, as indicated by arrow 30 in FIG. 5, to impart sliding, reciprocating, translating movement to the actuator 14 and to the external control tube 18 with respect to the hand grip 12 and the internal suction tube 16, to cause the forward portion of the external control tube 18 to engage and clear any surgical debris lodged in the entrance aperture 20 and to cause the forward portion of the control tube 18 to alternately cover and uncover various ones of the radially disposed suction holes to vary the effective size of the entrance aperture 20 to vary the suction applied to the surgical debris and, if desired, to focus the suction applied to the surgical debris at substantially the forward portion of the cylindrical filter. Upon the surgical suction apparatus of the present invention having the forward end of the external control tube 18 terminating in the annular cutter blade 21, and upon the above-noted sliding, reciprocating, translating movement being applied to the control tube 18, the cutter blade will engage and cut any surgical debris lodged in the radially disposed suction holes to enhance the clearing of the entrance aperture 20.

Referring now to FIG. 6, which as noted above is an enlarged partial view of the forward end of the internal control tube 16, it will be understood that in accordance with the further teachings of the present invention, the plurality of radially disposed suction holes 23 defining the entrance aperture 20 may be axially disposed such that the smaller holes are more forward of the suction tube 16 and the larger holes are more rearward of the suction tube. Accordingly, it will be understood that upon the control tube 18 being moved forwardly the suction may be focused at the end of the suction tube 16 by exposing only the smaller suction holes 23 or even portions thereof; conversely, upon the control tube 18 being moved rearwardly the number and size of the radially disposed suction holes 23 exposed are increased and the suction provided is accordingly increased. Further, it will be understood that the repetitive forward and rearward movement of the control tube 18 in the normal operation of the surgical suction device of the present invention will create a surging of the air sucked into the entrance aperture 20 thereby discouraging the build-up of surgical debris in the internal suction tube 16 and thereby further reducing the possibility of clogging.

Further, it will be understood that upon the operator moving the actuator 14 to its forwardmost position, thereby moving the control tube 18 to its forwardmost position, all of the radially disposed suction holes 23 will be completely covered thereby shutting off suction and preventing the attraction of bacteria laden air to the vicinity of the surgical suction apparatus and from the vicinity of a surgical wound. Still further, upon the surgical suction apparatus being removed from the operator's hand, while temporarily not in use, the shutting off of the suction will reduce, or eliminate, suction noise which may interfere with communication between those performing a surgical procedure.

It will be further understood that the thumb of the operator may be moved forwardly and rearwardly to move the actuator 14 and control tube 18 between its extreme rearward and forward positions shown, respectively, in FIGS. 4 and 5 and to stop the actuator 14 and control tube 18 at any intermediate position between the extreme rearward and forward positions.

As will be further understood by those skilled in the art, the above-described components comprising an embodiment of the present invention may be made of known materials and by known manufacturing processes. For example, the hand grip 12 and actuator 14 may be made of a suitable aluminum, or aluminum alloy, and may be manufactured, for example, by casting; the internal suction tube 16 and external control tube 18 may be made of a suitable stainless steel tubing or other suitable metal tubing. Alternatively, such components may be made of suitable plastics; for example, the hand grip 12 and actuator 14 may be made of a suitable plastic and may be manufactured, for example, by injection molding, and the internal suction tube 16 and external control tube 18 may be made of a suitable extruded plastic and the cutter blade 21 may be made of a suitable metal, such as stainless steel, and may be suitably secured to the end of the external control tube 18 by known metal-to-plastic adhesive techniques.

Referring now to FIGS. 7 through 10, a second embodiment of surgical suction apparatus structured according to the present invention is shown and designated generally by reference numeral 110.

Apparatus 110 includes a hand grip 112, an actuator 114 having a cutter blade 116 mounted thereon, a filter element 118 and an internal suction tube 120 (FIG. 7) slidably disposed within the control tube portion 122 of actuator 114. Handle section 112 and fluid barrel 120 are rigidly secured as is discussed below in detail. Actuator 114 is slidably mounted with respect to handle section 112 and internal suction tube 120 such as to permit selective positioning of actuator 114 with respect to internal suction tube 120 between the position shown in FIG. 5 and the position shown in FIG. 6, all as discussed below in detail.

Referring therefore to FIG. 7 it can be seen that handle section 112 includes a hand grip 124 having a fluid tube 126 extending therethrough. Fluid tube 126 extends outwardly of the lower wall 125 of hand grip 124 to define a connector element 128 which is ribbed to facilitate attachment to a flexible tube or other typical source of vacuum thereby defining an exit aperture for apparatus 110. Hand grip 124 is a hollow structure which is relieved at its upper end to permit slidable receipt of actuator 114 as is disclosed in detail below. The lower end of hand grip 124 is closed with the exception of an opening to permit through passage of fluid tube 126. In this regard, fluid tube 126 extends upwardly from connector element 128 through the closed end of hand grip 124 and through the hollow structure of the hand grip such as to extend above and beyond the upper extremities of the hand grip.

The upper inner surface of the forward wall of hand grip 124 is provided with a detent 125 which is provided to cooperate with the trigger 154 of actuator 114 to retain the suction device in suction mode as is discussed below in detail. It will also be recognized that the positioning of detent 125 is not critical, nor is the number of detents. Thus, plural detents formed on hand grip 124 and extending inwardly from the sides thereof may also be provided to co-operate with corresponding dimples in trigger 154 to achieve the same functional result.

At its upper end tube 126 is bent such as to extend generally perpendicularly to the major longitudinal axis of handle section 112. It should be noted that although the bend in tube 126 is disclosed to be a 90° bend in the embodiment of FIGS. 5 through 7, the angle defined by the axis of the major portion 130 and the minor portion 131 of tube 126 may be varied as desired in conjunction with variations in the angle defined by the major longitudinal axis of handle section 112 and the axis of barrel 120.

The end of minor portion 131 of tube 126 is provided with a plurality of spring fingers 134 which co-operate with a groove 135 formed in barrel 120 to rigidly secure internal suction tube 120 to fluid tube 126. More specifically, the major outside diameter of suction tube 120 is substantially equal to the inside diameter of fluid tube 126 so as to be slidably received therein. Formed adjacent the proximal end 138 of internal suction tube 120 is an annular groove 135. Thus, proximal end 138 of internal suction tube 120 may be slidably inserted within the minor portion 131 of fluid tube 126 until spring fingers 134 snap into place within groove 135 preventing withdrawal of the barrel. This procedure, of course, occurs during the assembly of apparatus 110 as is discussed below in detail.

The proximal end 1400 of internal suction tube 120 is relieved to define a second groove 142 and a reduced diameter annular shoulder 143. The outside diameter of shoulder 143 is substantially equal to the inside diameter of filter element 118 such that filter element 120 may be slidably received over internal suction tube 120. In this regard filter element 118 is a generally cylindrical member having a cylindrical wall 144 which is closed at one end by a plate 145. Formed in the other end of wall 144 are a plurality of spring fingers 146. Spring fingers 146 are positioned such that upon introduction of filter element 118 coaxially over the end of internal suction tube 120 the spring fingers are displaced radially outwardly by engagement with shoulder 143. Continued displacement of filter element 118 onto internal suction tube 120 permits spring fingers 146 to snap radially outward to engage the outer radial wall of second groove 142 whereby to preclude removal of filter element 118 from internal suction tube 120. The displacement of filter element 118 onto internal suction tube 120 is limited by the longitudinal width of second groove 142, i.e. by the positioning of the inner radial wall of second groove 142 with which the end of filter element 118 abuts upon complete insertion of the filter element.

It should also be noted that filter element 118 is provided with an entrance aperture which in the embodiment shown comprises a plurality of suction holes 150 which are sized and positioned in the same manner and for the same purposes as are discussed above with respect to suction holes 23 of the embodiment of FIGS. 1 through 6. Further, filter element 118 is provided with a longitudinally extending ridge 151 disposed on its outer surface. Ridge 151 cooperates with cutter blade 116 to preclude rotation thereof relative to the filter all as discussed below in detail.

Slidably disposed around and concentric with barrel 120 is control tube portion 122 of actuator 114. Actuator 114 includes the generally cylindrical barrel element or control tube 122, a trigger 154, a thumb piece mounting section 156 and a cutter blade mount 158. An opening 159 is formed between trigger 154 and thumb piece mounting section 156 to accommodate the passage therethrough of fluid tube 126.

The major portion of control tube 122 has an inside diameter which is substantially equal to the outside diameter of internal suction tube 120 to provide for concentric sliding therebetween. As best may be seen in FIG. 10, the distal end of control tube 122 is provided with a counterbore 160 which is coaxial with the longitudinal axis of control tube 122. The internal surface of counterbore 160 is relieved to define an annular groove 161 in which to receive the spring fingers 162 of cutter blade 116. The inner surface of control tube 122 is relieved adjacent its proximal end to define a radially extending shoulder 163 and an annular channel 164. In this regard the inside diameter of annular channel 164 is substantially equal to the outside diameter of fluid tube 126 with the minor portion 131 of which it has a sliding relationship.

The outer surface of internal suction tube 120, annular channel 164, shoulder 163 and the end of minor portion 131 of fluid tube 126 cooperate to define a cylindrical chamber 166 in which is received a coil spring 168. Coil spring 168 is sized in compression characteristic and length to exert a resistance to displacement of actuator 114 to the left as seen in FIGS. 5, 6 and 7, and to return actuator 114 to the position shown in FIGS. 5 and 7 upon release of trigger pressure.

Referring to FIG. 10, cutter blade 116 comprises a generally thin cylindrical member having split 169 extending axially throughout its length. The cutter blade 116 is provided with spring fingers 162 for cooperating with annular groove 161 to secure the blade within the end of control tube 122. Blade 116 is also provided with a machined cutting edge 179 which as shown, is angled outwardly and rearwardly from the end of filter element 118.

The inside diameter of cylindrical cutter blade 116 when not assembled to apparatus 110 is slightly smaller than the outside diameter of filter element 118 such as to establish a sliding-wiping engagement of the cutter over the outer surface of filter element 118 during operation. Because the split cylindrical cutter blade must be spread slightly to permit assembly over the filter element, the resiliency of the blade material, in tending to return to its natural configuration, i.e. with an inside diameter slightly smaller than the outside diameter of filter element 118, generates an inwardly directed pressure against the surface of filter element 118 so as to provide efficient wiping and cleaning of the surface of filter element 118 during operation. Thus, it can be seen from FIGS. 7 and 8 that displacement of actuator 114 from right to left causes a sliding of cutting edge 170 along the surface of filter element 118. In the event that any material such as bone chips or the like is lodged in suction holes 150, the motion of cutting edge 170 back and forth along filter element 118 severs such material thus clearing the holes and, effectively reactivating the filter element.

Thumb piece mounting section 156 comprises grooves 171 formed in the outer surfaces of actuator 114. Such grooves define locking means which receive spring fingers which are formed on inner surfaces of thumb piece 172 and which secure the thumb piece 172 in rigid engagement with actuator 114.

Formed in the lower surface of trigger 154 is a dimple 174. Dimple 174 is in axial alignment with detent 125 formed in the upper surface of hand grip 124 such that if actuator 114 is displaced from right to left as shown in FIGS. 7-9 by an amount sufficient to cause dimple 174 to overlay detent 125, actuator 114 is retained in the leftward or suctioning position until forced to the right by the exertion of pressure against thumb piece 172. The amount of force required to displace actuator 114 out of locked position is only that sufficient to overcome the resilient force generated by detent 125 against the lower surface of trigger 154.

Considering now the assembly of apparatus 110, the first step is to insert the proximal end 138 of internal suction tube 120 into minor portion 131 of fluid tube 126 until they are locked together through the cooperation of spring fingers 134 with groove 135. Filter element 118 is then secured to the distal end of fluid tube 126 by sliding its open end over annular shoulder 143 until spring fingers 146 are locked within groove 142. Spring 168 is then passed over internal suction tube 120 and positioned such as to engage the end of minor portion 131. Cutting blade 116 is then mounted in the end of control tube 122 by inserting the end of cutter blade 116 into counterbore 160 until spring fingers 162 snap into locking engagement within groove 161. In this regard care should be taken to position blade 116 such that its longitudinal split 169 is in approximate alignment with ridge 151 of filter element 118. This, of course, will facilitate ultimate alignment of the respective elements during assembly of the trigger section on the internal suction tube 120. With cutting blade 116 secured to mount 158 through the cooperation of spring fingers 162 with annular groove 161, actuator 114 including control tube 122 and cutter blade 116 is passed concentrically over internal suction tube 120 until it engages and compresses slightly spring 168 at approximately the position shown in FIG. 7. Thereafter, thumb piece 172 is snapped into position, the effect of which is to preclude disassembly of the apparatus.

In order to use apparatus 110, connector element 128 is secured to a suitable source of suction as is generally available in most operating rooms. Notwithstanding the suction connection, with the apparatus configured as shown in FIG. 5, little or no air or other material is caused to pass into filter element 116 through suction holes 150. However, when it is desired to increase suction, the surgeon squeezes trigger 154 thus displacing actuator 114 to the left against the force of spring 168. Such displacement uncovers suction holes 150 progressively. Thus, because of their sizes, the rate of suction of a fluid may be controlled by selectively uncovering suction holes 150. Material sucked through holes 150 into filter element 118 then passes through internal suction tube 120 into fluid tube 126 and, ultimately, out of apparatus 10 through the exit aperture of connector element 128.

As will be recognized by those who have used suctioning devices, clogging occurs from time to time. Such clogging may be the result of bone chips being caught in suction holes 150 or from any of a number of other reasons. This does not present a major problem in the operation of apparatus 110. More specifically, if a surgeon releases trigger 154 and spring 168 has insufficient force to cause trigger section 114 to return to the position shown in FIG. 5, then the surgeon may exert pressure on thumb piece 172 to manually displace actuator 114 to the desired position. Such pressure on thumb piece 172 generates a corresponding force on the cutting edge 170 of cutter 116 so as to sever whatever material is clogging suction holes 150 thereby to reestablish an unimpeded path for the flow of fluid and other materials through suction holes 150.

Thus, as can be seen by the foregoing, apparatus 110 may be utilized as a suctioning device throughout the course of a typical surgical procedure and without the need for substitution of suctioning devices as has been commonplace in the past. Fluid is removed when and if desired by the operation of actuator 114 to selectively uncover the apertures of filter element 118. If clogging occurs, the apertures may be cleared through the use of thumb piece 172 as discussed above.

Apparatus 110 may be manufactured using well known manufacturing techniques and materials which have been recognized in the art to be suitable for these purposes.

It will be understood by those skilled in the art that many modifications and variations may be made in the surgical suction apparatus of the present invention without departing from the spirit and the scope of the present invention.

What is claimed is:

1. Surgical suction apparatus for applying suction to surgical debris to clear a surgical wound, said apparatus for being connected to a suction source, comprising:
   suction means including a first tube terminating at its forward and in a generally cylindrical filter provided with a plurality of radially disposed suction holes providing an entrance aperture through which said suction is applied to said surgical debris and terminating at its rearward end in an exit aperture through which surgical debris sucked through said entrance aperture exits said apparatus, and control means including a second tube coaxially surrounding said first tube and mounted for sliding, reciprocating, translating movement relative to said first tube to permit portions of said second tube to engage any surgical debris lodged in said entrance aperture to clear said entrance aperture and to permit portions of said second tube to alternately cover and uncover said suction holes to vary the effective size of said entrance aperture.

2. Surgical apparatus according to claim 1 wherein said plurality of radially disposed suction holes are of different sizes and are axially disposed such that the smaller sized suction holes are forwardly of said generally cylindrical filter and said larger suction holes are rearwardly of said generally cylindrical filter whereby, upon said second tube being slid forwardly of said first tube, the number and size of said radially disposed suction holes exposed are decreased thereby reducing the suction applied and focusing the suction at the forward end of said first tube and, upon said second tube being slid rearwardly of said first tube, the size and number of said radially disposed suction holes exposed are increased thereby increasing the suction applied.

3. Surgical apparatus according to claim 1 wherein said second tube is terminated in a generally annular cutting blade for cutting any surgical debris lodged in said suction hole to enhance the clearing of said entrance aperture.

4. Surgical suction apparatus according to claim 1 including closure means for urging said second tube into position to cover said suction holes.

5. Surgical suction apparatus according to claim 4 including means for retaining said second tube in position wherein said suction holes are uncovered notwithstanding the urging of said closure means.

6. Surgical suction apparatus for applying suction to surgical debris to clear a surgical wound, said apparatus for being connected to a suction source, comprising:
suction means including a first tube terminating at its forward end in a generally cylindrical filter provided with a plurality of radially disposed suction holes providing an entrance aperture through which said suction is applied to said surgical debris and terminating at its rearward end in an exit aperture through which said surgical debris sucked through said entrance aperture exits said apparatus, and
control means including a second tube coaxially surrounding said first tube and mounted for sliding, reciprocating, translating movement relative to said first tube to permit portions of said second tube to engage and clear any surgical debris lodged in said entrance aperture.

7. Surgical apparatus according to claim 6 wherein said second tube is terminated in a generally annular cutting blade for cutting any surgical debris lodged in said entrance aperture to enhance the clearing of said entrance aperture.

8. Surgical suction apparatus according to claim 6 wherein said second tube is displaceable in a first direction and in a second opposed direction during said sliding, reciprocating, translating movement, and including means for exerting a force to urge said second tube in said first direction.

9. Surgical suction apparatus according to claim 8 including means for maintaining said second tube displaced in said second opposed direction against the force of said means for exerting a force.

10. Surgical suction apparatus for applying suction to surgical debris to clear a surgical wound, said apparatus for being connected to a suction source, comprising:
suction means including a first tube terminating at its forward end in a generally cylindrical filter provided with a plurality of radially disposed suction holes providing an entrance aperture through which said suction is applied to said surgical debris and terminating at its rearward end in an exit aperture through which said surgical debris sucked through said entrance aperture exits said apparatus, and
control means including a second tube coaxially surrounding said first tube and mounted for sliding, reciprocating translating movement relative to said first tube to permit portions of said second tube to cover and uncover said suction holes to vary the suction applied to said surgical debris.

11. Surgical apparatus according to claim 10 wherein said plurality of radially disposed suction holes are of different sizes and are axially disposed such that the smaller sized suction holes are forwardly of said generally cylindrical filter and said larger suction holes are rearwardly of said generally cylindrical filter whereby, upon said second tube being slid forwardly of said first tube, the number and size of said radially disposed suction holes exposed are decreased thereby reducing the suction applied and focusing the suction at the forward end of said first tube and, upon said second tube being slid rearwardly of said first tube, the size and number of said radially disposed suction holes exposed are increased thereby increasing the suction applied.

12. Surgical suction apparatus according to claim 10 wherein said second tube is displaceable in a first direction and in a second opposed direction during said sliding, reciprocating, translating movement, and including means for exerting a force to urge said second tube in said first direction.

13. Surgical suction apparatus according to claim 12 including means for maintaining said second tube displaced in said second opposed direction against the force of said means for exerting a force.

* * * * *